United States Patent
Miura

(10) Patent No.: US 8,906,980 B2
(45) Date of Patent: Dec. 9, 2014

(54) WATER-SOLUBLE POLYMER COMPOSITION, COMPOSITION FOR FORMING PLASTER LAYER OF SKIN PATCH, AND SKIN PATCH

(75) Inventor: Kazuyuki Miura, Himeji (JP)

(73) Assignee: Sumitomo Seika Chemicals Co., Ltd, Kako-Gun, Hyogo (JP)

( * ) Notice: Subject to any disclaimer, the term of this patent is extended or adjusted under 35 U.S.C. 154(b) by 166 days.

(21) Appl. No.: 13/383,242

(22) PCT Filed: Jul. 22, 2010

(86) PCT No.: PCT/JP2010/062220
§ 371 (c)(1),
(2), (4) Date: Jan. 10, 2012

(87) PCT Pub. No.: WO2011/013546
PCT Pub. Date: Feb. 3, 2011

(65) Prior Publication Data
US 2012/0123015 A1    May 17, 2012

(30) Foreign Application Priority Data
Jul. 30, 2009   (JP) ................................. 2009-177281

(51) Int. Cl.
*C08L 33/02* (2006.01)
*C08K 5/17* (2006.01)
*A61M 35/00* (2006.01)
*C09K 5/08* (2006.01)
*C08K 5/00* (2006.01)
*A61K 9/70* (2006.01)

(52) U.S. Cl.
CPC .............. *A61K 9/7061* (2013.01); *A61M 35/00* (2013.01); *C08L 33/02* (2013.01); *C09K 5/08* (2013.01); *C08K 5/0008* (2013.01); *A61K 9/7084* (2013.01); *Y10S 524/916* (2013.01)
USPC ............ 523/111; 524/239; 524/845; 524/916

(58) Field of Classification Search
USPC ............................. 523/111; 524/239, 845, 916
See application file for complete search history.

(56) References Cited

U.S. PATENT DOCUMENTS

| | | | | |
|---|---|---|---|---|
| 5,480,649 | A  * | 1/1996 | Akazawa et al. | 424/449 |
| 6,034,172 | A  * | 3/2000 | Muller et al. | 524/803 |
| 7,230,061 | B2 * | 6/2007 | Shioji et al. | 526/328 |
| 2003/0165560 | A1 * | 9/2003 | Otsuka et al. | 424/445 |
| 2003/0170592 | A1 * | 9/2003 | Chadwick et al. | 433/215 |
| 2004/0072715 | A1 * | 4/2004 | Griese et al. | 510/405 |
| 2010/0254928 | A1 * | 10/2010 | Yamazaki et al. | 424/70.1 |

FOREIGN PATENT DOCUMENTS

| | | |
|---|---|---|
| JP | 2-311549 | 12/1990 |
| JP | 3-188149 | 8/1991 |
| JP | 7-48281 * | 2/1995 |
| JP | 407048281 A * | 2/1995 |
| JP | 2000-318096 | 11/2000 |
| JP | 2007-119552 A1 | 5/2007 |
| JP | 2009-161618 A1 | 7/2009 |
| WO | WO 2006/112533 A1 | 10/2006 |
| WO | WO 2007/126067 A1 | 11/2007 |

OTHER PUBLICATIONS

Brochure for Carbopol by ADMIX, Downloaded on Sep. 16, 2013.*
International Search Report for International Application No. PCT/JP2010/062220 dated Aug. 24, 2010.

* cited by examiner

*Primary Examiner* — Tae H Yoon
(74) *Attorney, Agent, or Firm* — Kratz, Quintos & Hanson, LLP

(57) ABSTRACT

The present invention relates to a water-soluble polymer composition which comprises a water-soluble poly(meth)acrylic polymer and a gelation rate retarding agent, and a composition for forming a plaster layer of a skin patch which is obtainable by adding a polyvalent metal compound to the water-soluble polymer composition. When a polyvalent metal compound is added, the aforesaid water-soluble polymer composition shows an appropriate induction period before the start of the hardening of the gel. When the water-soluble polymer composition is used for forming a plaster layer of a skin patch, therefore, additive ingredients can be uniformly mixed and the procedure for coating to a support can be facilitated.

4 Claims, No Drawings

WATER-SOLUBLE POLYMER COMPOSITION, COMPOSITION FOR FORMING PLASTER LAYER OF SKIN PATCH, AND SKIN PATCH

TECHNICAL FIELD

The present invention relates to a water-soluble polymer composition, a composition for forming a plaster layer of a skin patch, production methods therefor, and a skin patch prepared using the composition for forming a plaster layer.

BACKGROUND ART

A poultice, cooling sheet, or like skin patch is produced by applying a gel-like plaster, which has been prepared by adding various medicaments, water, or other ingredients to a composition containing a water-soluble polymer, to the surface of a nonwoven fabric or like support, and curing and aging the composition, thereby forming the plaster layer on the support. Examples of water-soluble polymers that may be added to such a composition include poly(meth)acrylic polymers, such as poly(meth)acrylic acid or a salt thereof.

A composition for forming a plaster layer that contains a water-soluble polymer and that is used for a skin patch is required to have sufficient adhesiveness to the skin, elasticity for application to a bending part, and other properties. It is also required to have various other properties adopted to the skin patch production process.

A typical process for producing a poultice or cooling sheet comprises the steps of preparing a gel-like plaster by mixing various additive ingredients to a composition containing a water-soluble polymer, applying the gel-like plaster to a nonwoven fabric or like support, covering the surface thereof with a polyethylene film or like liner, cutting and packing the result, and then curing and aging the composition in the pack.

In such a method, when a gel-like plaster is prepared from the water-soluble polymer composition, aluminum or a like polyvalent metal compound is added to the water-soluble polymer composition as a cross linking agent. If the water-soluble polymer easily reacts with the polyvalent metal compound and the curing speed is too fast, gelation proceeds during the application of the water-soluble polymer to the support, making it difficult to apply it to the support. Therefore, in order to control the reaction speed between the water-soluble polymer and the polyvalent metal compound, a method is employed wherein disodium ethylenediaminetetraacetate is also added as a gelation rate retarding agent when adding the polyvalent metal compound (Patent Literature 1).

CITATION LIST

Patent Literature

PTL 1: Japanese Unexamined Patent Publication No. H03-188149

SUMMARY OF INVENTION

Technical Problem

However, it is difficult to control the curing speed of the gel by the method disclosed in PTL 1 wherein a polyvalent metal compound and a gelation rate retarding agent are added simultaneously. This makes it difficult to obtain a desirable curing speed, and may hinder operations such as mixing additive ingredients and applying the plaster to a support.

The present invention was made in view of the current status of conventional techniques described above. One of the main objects thereof is to provide a composition that is usable in forming a plaster layer for a skin patch, such as a poultice, a cooling sheet, or the like. More specifically, the present invention aims to provide a composition containing a water-soluble polymer for which the gelation speed is easily controllable and which can readily be applied to a support, and a skin patch formed by using the composition.

Solution to Problem

The present inventors conducted extensive research to achieve the above objects. As a result, they found that when a polyvalent metal compound as a cross linking agent is added to a water-soluble polymer composition containing a gelation rate retarding agent together with poly(meth)acrylic acid or a salt thereof, and the resulting composition is used as a composition for forming a plaster layer of a skin patch, the gelation speed of the gel-like plaster can be easily controlled and the induction period until the hardening of the gel-like plaster proceeds can be desirably arranged. This facilitates the operation of mixing additive ingredients with the composition and applying the plaster to a support. The present invention has been accomplished based on the above findings.

Specifically, the present invention provides a water-soluble polymer composition, a composition for forming a plaster layer of a skin patch, production methods thereof, and a skin patch prepared using the composition for forming a plaster layer, as described below.

Item 1. A water-soluble polymer composition comprising a water-soluble poly(meth)acrylic polymer and a gelation rate retarding agent.

Item 2. The water-soluble polymer composition according to Item 1, which is prepared by polymerizing at least one (meth)acrylic compound selected from the group consisting of (meth)acrylic acid and salts thereof to obtain a hydrated gel of a water-soluble poly(meth)acrylic polymer, adding a gelation rate retarding agent before or while drying the resulting hydrated gel, and drying the result.

Item 3. The water-soluble polymer composition according to Item 1 or 2, wherein the amount of the gelation rate retarding agent added is 0.1 to 10 parts by mass relative to 100 parts by mass of the (meth)acrylic compound, which is at least one compound selected from the group consisting of (meth)acrylic acid and salts thereof, that is used to prepare the water-soluble poly(meth)acrylic polymer.

Item 4. A composition for forming a plaster layer of a skin patch comprising the water-soluble polymer composition of any one of Items 1 to 3 and a polyvalent metal compound.

Item 5. The composition for forming a plaster layer according to Item 4, wherein the amount of the polyvalent metal compound is 0.01 to 20 parts by mass relative to 100 parts by mass of the water-soluble polymer composition.

Item 6. A skin patch comprising a plaster layer formed from the composition for forming a plaster layer of Item 4 or 5.

Item 7. The skin patch according to Item 6, which is a poultice or a cooling sheet.

Item 8. A method for producing a water-soluble polymer composition comprising:

polymerizing at least one (meth)acrylic compound selected from the group consisting of (meth)acrylic acid and salts thereof to obtain a hydrated gel of a water-soluble poly(meth)acrylic polymer;

adding a gelation rate retarding agent before or while drying the resulting hydrated gel; and drying the result.

Item 9. A method for producing a composition for forming a plaster layer of a skin patch comprising a step of adding a polyvalent metal compound to the water-soluble polymer composition obtainable by the method of Item 8.

The water-soluble polymer composition and the composition for forming a plaster layer of a skin patch of the present invention are explained in detail below.

(I) Water-Soluble Polymer Composition

The water-soluble polymer composition of the present invention comprises a water-soluble poly(meth)acrylic polymer and a gelation rate retarding agent as active ingredients. The water-soluble poly(meth)acrylic polymer and gelation rate retarding agent contained in the composition are explained below.

(1) Water-Soluble Poly(meth)acrylic polymer

There is no limitation to the water-soluble poly(meth) acrylic polymer used in the present invention as long as it is obtainable by using at least one (meth)acrylic compound selected from the group consisting of (meth)acrylic acid and salts thereof as a monomer component and polymerizing it. The polymerization method is not particularly limited, and typical methods for polymerizing a (meth)acrylic compound, such as a reversed-phase suspension polymerization method or an aqueous solution polymerization method, can be employed. Preferable examples of polymerization methods include those in which the polymerization degree is controlled when polymerizing a monomer component so that extremely low-molecular-weight polymers and extremely high-molecular-weight polymers are not formed. In this specification, "(meth)acrylic acid" includes both "acrylic acid" and "methacrylic acid."

Hereunder, the reversed-phase suspension polymerization method and the aqueous solution polymerization method are explained in detail as examples for producing a water-soluble poly(meth)acrylic polymer.

(i) Reversed-Phase Suspension Polymerization Method

The reversed-phase suspension polymerization method is conducted by, for example, subjecting at least one (meth) acrylic compound selected from the group consisting of (meth)acrylic acid and salts thereof as a monomer component to water-in-oil reversed-phase suspension polymerization using a radical polymerization initiator in a petroleum hydrocarbon dispersion medium that contains at least one component selected from the group consisting of surfactants and polymeric dispersion agents. The reversed-phase suspension polymerization method may be conducted in two or more steps, wherein a (meth)acrylic compound is further added to a slurry of a water-soluble poly(meth)acrylic polymer obtained by reversed-phase suspension polymerization.

The (meth)acrylic compound used as the monomer component is generally used in the form of an aqueous solution. The concentration of the (meth)acrylic compound in the aqueous solution is preferably 15 mass % to a saturated concentration in order to quickly advance the polymerization reaction.

In the present invention, in order to render an appropriate water-soluble property to the resulting poly(meth)acrylic polymer, it is preferable that a (meth)acrylic acid salt be used singly or a mixture of a (meth)acrylic acid salt and (meth) acrylic acid be used as the (meth)acrylic compound that is used as the monomer component. A poly(meth)acrylic polymer having an appropriate water-soluble property can be produced by, for example, neutralizing a part or all of the (meth)acrylic acid in an aqueous solution using a base to prepare an aqueous solution containing (meth)acrylic acid salt, and causing a polymerization reaction in the aqueous solution. In this case, the neutralization degree of the (meth) acrylic acid is preferably about 5 to 100 mol %, and more preferably about 20 to 100 mol % in order to obtain a satisfactory solubility of the resulting water-soluble poly(meth) acrylic polymer.

Specific examples of salts of (meth)acrylic acid include lithium (meth)acrylate, sodium (meth)acrylate, potassium (meth)acrylate, and ammonium (meth)acrylate. Among these salts of (meth)acrylic acid, sodium (meth)acrylate and potassium (meth)acrylate are preferable, and sodium (meth)acrylate is particularly preferable. In order to prepare such salts of (meth)acrylic acid, bases such as lithium hydroxide, sodium hydroxide, potassium hydroxide, and ammonia can be used.

Examples of radical polymerization initiators include potassium persulfate, ammonium persulfate, sodium persulfate, and like persulfates; methyl ethyl ketone peroxide, methyl isobutyl ketone peroxide, di-tert-butyl peroxide, tert-butyl cumyl peroxide, tert-butyl peroxyacetate, tert-butyl peroxyisobutyrate, tert-butyl peroxypivalate, hydrogen peroxide, and like peroxides; and 2,2'-azobis(2-amidinopropane) dihydrochloride, 2,2'-azobis[2-(N-phenylamidino)propane] dihydrochloride, 2,2'-azobis[2-(N-allylamidino)propane] dihydrochloride, 2,2'-azobis{2-[1-(2-hydroxyethyl)-2-imidazolin-2-yl]propane}dihydrochloride, 2,2'-azobis{2-methyl-N-[1,1-bis(hydroxymethyl)-2-hydroxyethyl] propionamide}, 2,2'-azobis[2-methyl-N-(2-hydroxyethyl)-propionamide], 4,4'-azobis(4-cyanovaleric acid), and like azo compounds. These radical polymerization initiators may be used singly or in a combination of two or more. Among these radical polymerization initiators, potassium persulfate, ammonium persulfate, sodium persulfate and 2,2'-azobis(2-amidinopropane)dihydrochloride are suitably used as they are easily available from an industrial perspective and have good storage stability.

The amount of radical polymerization initiator used is preferably 0.015 to 0.15 parts by mass relative to 100 parts by mass of (meth)acrylic compound in order to shorten the polymerization reaction time, prevent an excessively rapid polymerization reaction, and easily control the degree of polymerization as desired. When the amount of radical polymerization initiator used is too small, the polymerization reaction may be undesirably prolonged. When the amount of radical polymerization initiator used is too large, the polymerization reaction proceeds too quickly, resulting in an excessively rapid reaction. This may make it impossible to control the polymerization reaction.

The radical polymerization initiator may be used as a redox-polymerization initiator in combination with sodium sulfite, sodium hydrogensulfite, ferrous sulfite, and like sulfites; D-ascorbic acid, L-ascorbic acid, rongalite, and like reducing agents; etc.

When the poly(meth)acrylic polymer is produced by the method described above, the addition of a water-soluble chain transfer agent is preferable in order to control the degree of polymerization so that the formation of an extremely low-molecular-weight polymer or an extremely high-molecular-weight polymer can be prevented. Examples of water-soluble chain transfer agents include hypophosphite compounds, phosphorous compounds, thiol compounds, secondary alcohol compounds, and amine compounds. These water-soluble chain transfer agents may be used singly or in a combination of two or more. Among these water-soluble chain transfer agents, sodium hypophosphite, potassium hypophosphite, and like hypophosphite compounds are suitably used because they have no odor and are desirable in terms of sanitary and safety aspects.

In order to suitably control the degree of polymerization, the amount of water-soluble chain transfer agent used is preferably 0.001 to 2 parts by mass, and more preferably 0.001 to 1.7 parts by mass relative to 100 parts by mass of (meth) acrylic compound. When the amount of water-soluble chain transfer agent used is too small, the effect of the water-soluble chain transfer agent may not be fully exhibited. When the amount of water-soluble chain transfer agent used is too large, the proportion of the low-molecular-weight polymer undesirably increases and the gel curing rate of the composition for forming a plaster layer tends to become slow. Furthermore, when a poultice is produced using this composition, the adhesiveness of the gel of the poultice may be lowered because the salt content in the gel increases.

Examples of surfactants used for polymerizing a (meth) acrylic compound include polyglyceryl fatty acid esters, sucrose fatty acids esters, sorbitan fatty acid esters, polyoxyethylenesorbitan fatty acid esters, polyoxyethyleneglycerine fatty acid esters, sorbitol fatty acid esters, polyoxyethylenesorbitol fatty acid esters, polyoxyethylene alkyl ether, polyoxyethylene alkyl phenyl ether, polyoxyethylene castor oil, polyoxyethylene hydrogenated castor oil, alkyl allyl formaldehyde condensed polyoxyethylene ethers, polyoxyethylene polyoxypropylene block copolymers, polyoxyethylene polyoxypropyl alkyl ethers, polyethyleneglycol fatty acid esters, polyoxyethylene alkylamine, phosphoric esters of polyoxyethylene alkyl ether, and phosphoric esters of polyoxyethylene alkyl allyl ether. These surfactants may be used singly or in a combination of two or more. Among these surfactants, sorbitan fatty acid esters, polyglyceryl fatty acid esters, and sucrose fatty acid esters are suitably used as they can render excellent dispersion stability to the aqueous solution containing the (meth)acrylic compound.

Examples of polymeric dispersion agents include maleic anhydride modified polyethylene, maleic anhydride modified polypropylene, maleic anhydride modified ethylene/propylene copolymers, maleic anhydride modified EPDM (ethylene/propylene/diene terpolymers), maleic anhydride modified polybutadiene, ethylene/maleic anhydride copolymers, ethylene/propylene/maleic anhydride copolymers, butadiene/maleic anhydride copolymers, oxidized polyethylene, ethylene/acrylic acid copolymers, ethylcellulose, and ethylhydroxyethyl cellulose. These polymeric dispersion agents may be used singly or in a combination of two or more. Among these, maleic anhydride modified polyethylene, maleic anhydride modified polypropylene, maleic anhydride modified ethylene propylene copolymers, oxidized polyethylene, and ethylene/acryl acid copolymers are suitably used as they can render excellent dispersion stability to the aqueous solution containing the (meth)acrylic compound.

Both or only one of the surfactant and polymeric dispersion agent may be used. The amount of these components used i.e., the total amount of surfactant and polymeric dispersion agent, is preferably 0.1 to 5 parts by mass and more preferably 0.2 to 3 parts by mass relative to 100 parts by mass of (meth)acrylic compound in order to maintain excellent dispersed state of an aqueous solution containing the (meth)acrylic compound, and to obtain a dispersion effect that achieves a good balance with the amount of these components used. When the amount of these components used is too small, the dispersibility of the (meth)acrylic compound becomes undesirably low, and this may result in irregular polymerization. When the amount of these components used is too large, a dispersion effect that is in good balance with the amount used may not be achieved.

Examples of petroleum hydrocarbon dispersion mediums include n-hexane, n-heptane, n-octane, ligroin, and like aliphatic hydrocarbons; cyclopentane, methylcyclopentane, cyclohexane, methylcyclohexane, and like alicyclic hydrocarbons; and benzene, toluene, xylene, and like aromatic hydrocarbons. These petroleum hydrocarbon dispersion mediums may be used singly or in a combination of two or more. Among these petroleum hydrocarbon dispersion mediums, n-hexane, n-heptane, and cyclohexane are preferable as they are easily available from an industrial perspective, stable in quality and inexpensive.

The amount of petroleum hydrocarbon dispersion medium used is preferably 50 to 600 parts by mass, and more preferably 80 to 550 parts by mass relative to 100 parts by mass of (meth)acrylic compound in order to easily control the polymerization temperature by removing the heat of polymerization.

The reaction temperature in the polymerization varies depending on the radical polymerization initiator used. The reaction temperature is preferably about 20 to 110° C. Having a reaction temperature within that range facilitates rapid polymerization to shorten the polymerization time, improves productivity, and allows easy removal of the polymerization heat to promote a smooth reaction. The reaction temperature is more preferably about 40 to 90° C. in order to easily control the polymerization temperature and degree of polymerization. When the reaction temperature is too low, the rate of polymerization becomes slow and prolongs the polymerization time, and is thus economically undesirable. When the reaction temperature is too high, removal of the polymerization heat becomes difficult. This may make it difficult to achieve a smooth reaction.

After the polymerization reaction is thus completed, a slurry is obtained in which a hydrated gel of water-soluble poly(meth)acrylic polymer is dispersed therein. Thereafter, water and the petroleum hydrocarbon dispersion medium are removed by heating, for example, at 80 to 200° C., to dry the resulting slurry, obtaining a water-soluble poly(meth)acrylic polymer.

(ii) Aqueous Solution Polymerization Method

An aqueous solution polymerization method is explained below as one embodiment. The aqueous solution polymerization method can be performed according to a conventional method using, for example, a (meth)acrylic compound as a monomer component, and a radical polymerization initiator.

In the aqueous solution polymerization method, the types, amounts, etc., of the (meth)acrylic compound, radical polymerization initiator, other optional components, and the like are the same as those used in the reversed-phase suspension polymerization method explained above.

In the aqueous solution polymerization method, the reaction temperature, reaction time, and the like during the polymerization reaction are the same as those of the reversed-phase suspension polymerization method explained above.

After the polymerization reaction is completed, a hydrated gel of water-soluble poly(meth)acrylic polymer is obtained. Thereafter, water is removed and the hydrated gel is dried by heating, for example, at 80 to 200° C., to obtain a water-soluble poly(meth)acrylic polymer.

(2) Gelation Rate Retarding Agent

In the present invention, compounds having a chelation ability or a coordination ability with regard to metal ions can be used as a gelation rate retarding agent. There is no limitation to the gelation rate retarding agents, and known compounds usable as a gelation rate retarding agent for a poly (meth)acrylic polymer can be used. Examples thereof include organic acids such as ethylenediaminetetraacetic acid, diethylenetriaminepentaacetic acid, acetic acid, citric acid, fumaric acid, tartaric acid, lactic acid, and malic acid; salts of these organic acids; inorganic acids such as boric acid and carbonic acid; and salts of inorganic acids, such as borate, carbonate, and hydrogen carbonate. There is no particular limitation to the types of the organic acid salts and inorganic acid salts as long as they are water soluble, and examples thereof include alkali metal salts, alkaline earth metal salts, and ammonium salts.

These gelation rate retarding agents may be used singly or in a combination of two or more. Among these gelation rate retarding agents, ethylenediaminetetraacetic acid and salts thereof are suitably used because they have no odor and are desirable in terms of sanitary and safety aspects.

The amount of the gelation rate retarding agent added is preferably about 0.1 to 10 parts by mass relative to 100 parts by mass of the (meth)acrylic compound used as a monomer component to attain the appropriate induction period for hardening the gel. When the amount of the gelation rate retarding agent is too small, an induction period sufficient for fully kneading the additive ingredients added to the composition may not be attained when poultices or the like are produced using the composition containing the water-soluble poly(meth)acrylic polymer. In case that the amount of the gelation rate retarding agent is too large, when a polyvalent metal compound is added to the composition as a cross linking agent to form a gel-like plaster, the masking action to the polyvalent metal ions is too strong and the gelation reaction is readily hindered. This tends to prolong the gelation time and is thus not efficient; furthermore, the final strength of the formed plaster layer may become undesirably low.

(3) Method for Producing a Water-Soluble Polymer Composition

The water-soluble polymer composition of the present invention comprises the water-soluble poly(meth)acrylic polymer and the gelation rate retarding agent described above as active ingredients. By forming a composition comprising a water-soluble poly(meth)acrylic polymer and a gelation rate retarding agent in advance, the water-soluble polymer and the gelation rate retarding agent are present in a uniform manner.

This allows the curing speed to be easily controlled when such a composition is reacted with a polyvalent metal compound used as a cross linking agent. Therefore, when a plaster layer for a skin patch is formed by adding a polyvalent metal compound to promote gelation, a desirable induction period can be attained before the initiation of the hardening of the gel-like composition. As a result, this causes the additive ingredients to be uniformly mixed and facilitates the application of the composition to a support.

The method for mixing the water-soluble poly(meth)acrylic polymer with the gelation rate retarding agent is not particularly limited as long as it can mix the water-soluble poly(meth)acrylic polymer with the gelation rate retarding agent as uniformly as possible.

Examples of such methods include: polymerizing a (meth)acrylic compound in the presence of the gelation rate retarding agent during the polymerization process of the poly(meth)acrylic polymer described above; and polymerizing a (meth)acrylic compound to form a hydrated gel of poly(meth)acrylic polymer, and adding a gelation rate retarding agent before or while drying the hydrated gel. By using such methods, the water-soluble polyacrylic polymer and the gelation rate retarding agent can be mixed. In particular, in order to smoothly conduct the polymerization reaction for the poly(meth)acrylic polymer, the water-soluble polymer composition of the present invention is preferably produced by a method comprising polymerizing the (meth)acrylic compound to prepare a hydrated gel, then adding a gelation rate retarding agent to the resulting hydrated gel, and drying the result, or adding a gelation rate retarding agent while drying the hydrated gel.

(II) Composition for Forming a Plaster Layer of a Skin Patch

A composition prepared by adding a polyvalent metal compound, as a cross linking agent, to the water-soluble polymer composition comprising the water-soluble poly(meth)acrylic polymer and gelation rate retarding agent described above has a property such that gelation gradually proceeds. Such a composition can be used for forming a plaster layer of a skin patch. A plaster layer of a skin patch can be formed by, for example, applying a gel-like composition, which has been obtained by adding a polyvalent metal compound, to a support for a skin patch, and then curing and aging it.

A polyvalent metal compound added to the composition for forming a plaster layer functions as a cross-linking agent to the water-soluble poly(meth)acrylic polymer. Examples of polyvalent metal compounds include salts of bivalent to hexavalent metal ions with anions, such as chloride ions, sulphate ions, silicate ions, and phosphate ions. Specific examples of polyvalent metal ions include aluminum ions, calcium ions, iron ions and the like. Specific examples of polyvalent metal compounds include aluminum hydroxide, aluminum sulfate, aluminum silicate, aluminum phosphate, aluminum glycinate, calcium hydroxide, and ferric sulfate. These polyvalent metal compounds may be used singly or in a combination of two or more.

The amount of the polyvalent metal compound added is preferably about 0.01 parts by mass or more, more preferably 0.05 parts by mass or more, and particularly preferably 0.1 parts by mass or more relative to 100 parts by mass of the water-soluble poly(meth)acrylic polymer in order to render excellent shape retention to the plaster layer to be prepared by applying the gel-like plaster formed from a composition, to which a polyvalent metal compound has been added, to a support, followed by curing and aging. The upper limit of the amount of the polyvalent metal compound used is preferably about 20 parts by mass or less, more preferably 15 parts by mass or less, and particularly preferably about 10 parts by mass or less relative to 100 parts by mass of water-soluble poly(meth)acrylic polymer in order to render excellent elasticity and adhesiveness to the plaster layer to be formed.

In addition to the water-soluble poly(meth)acrylic polymer composition and polyvalent metal compound, polyhydric alcohols, pH adjusters and the like may be added to the composition for forming a plaster layer of a skin patch according to the present invention.

Among these, the polyhydric alcohols function as a water retention agent. Specific examples of polyhydric alcohols include glycerol, polypropylene glycol, sorbitol, and butylene glycol. These polyhydric alcohols may be used singly or in a combination of two or more.

The amount of the polyhydric alcohol is preferably 50 mass % or less relative to the total amount of the composition for forming a plaster layer, including polyhydric alcohol, water, other optional additive ingredients, and the like. If the amount of the polyhydric alcohol exceeds 50 mass %, the curing speed may be undesirably lowered when the gel-like plaster is formed into a plaster layer by applying it to a support, followed by curing and aging.

The pH adjuster promotes the separation of metal ions from a polyvalent metal compound and functions as a pH-controlling agent for a composition for forming the plaster layer itself. Specific examples of pH adjusters include tartaric acid, lactic acid, citric acid, and like organic acids. The pH adjusters may be used singly or in a combination of two or more. The amount of the pH adjuster is preferably such that when a composition for forming a plaster layer is obtained by adding water, polyhydric alcohol, other optional additive ingredients, and the like, the resulting composition has a pH of about 3 to 7.

The composition for forming a plaster layer of the present invention comprises the components described above. The composition is usually used in the form of an aqueous dispersion by adding water thereto. There is no particular limitation to the method for preparing the composition, and the composition can be prepared, for example, as follows. A polyhydric alcohol is added, as necessary, to a polyvalent metal compound and a water-soluble polymer composition containing a gelation rate retarding agent, and then these components are mixed to prepare a dispersion. Separate from this dispersion, an aqueous solution in which a pH adjuster and water are mixed is prepared. Thereafter, the dispersion prepared above is mixed with the aqueous solution to obtain the composition for forming a plaster layer.

The amount of water used is not particularly limited. The preferable amount of water is 50 mass % or more relative to the total amount of the composition for forming a plaster layer including water, polyhydric alcohol, other optional additive ingredients, etc. When the amount of water is less than 50 mass %, the application of the gel-like plaster to a support may become difficult, and the curing speed may become difficult to control when a plaster layer is formed by curing and aging the gel-like plaster.

(III) Skin Patch

A skin patch can be obtained as follows. A polyvalent metal compound, as a cross linking agent, and optional additive ingredients, if necessary, are added to the aforementioned water-soluble polymer composition comprising a water-soluble poly(meth)acrylic polymer and a gelation rate retarding agent to form a gel-like plaster. The gel-like plaster is then applied to a nonwoven fabric or like support, and the result is subjected to curing and aging to form a plaster layer, thereby obtaining a skin patch. Specific examples of skin patches include poultices and cooling sheets.

The method for producing a skin patch is not particularly limited, and may, for example, comprise the steps of adding a polyvalent metal compound and optional additives to the water-soluble polymer composition of the present invention to prepare a gel-like composition, applying the gel-like composition to a nonwoven fabric or like support, covering the surface thereof with a polyethylene film or like liner, cutting the result into a desirable size if necessary, packing the result, and curing and aging the gel in the pack.

The additives may be suitably selected from known components depending on the application of the skin patch. Examples of additives for producing a poultice include methyl salicylate, L-menthol, D,L-camphor, and tocopheryl acetate. Examples of additives for producing a cooling sheet include paraben, a pigment, and a fragrance. The amounts of these additives may be the same as those of general plaster layers.

A polyester nonwoven fabric is an example of a nonwoven fabric that is used as a support. Nonwoven fabrics are commercially available, such as a plaster base fabric (produced by Japan Vilene Company, Ltd.).

Advantageous Effects of Invention

The composition prepared by adding a polyvalent metal compound to the water-soluble polymer composition of the present invention has an appropriate induction period before the start of the hardening of the gel. Therefore, when additive ingredients are added to the composition to prepare a gel-like plaster, the additive ingredients can be smoothly and uniformly mixed with the composition. This also allows the gel-like plaster to be easily applied to a support.

DESCRIPTION OF EMBODIMENTS

The present invention is explained in detail below with reference to Examples and Comparative Examples. However, the scope of the invention is not limited to these Examples.

Example 1

Preparation of a Water-Soluble Polymer Composition

A 1,000-mL five-necked cylindrical round-bottom flask equipped with a reflux condenser, a dropping funnel, a nitrogen introduction tube, a stirrer, and a stirring blade was prepared. n-Heptane (340 g) was placed in this flask, and 0.92 g of sucrose stearate having HLB of 3 (produced by Mitsubishi-Kagaku Foods Corporation, Ryoto Sugar Ester S-370) and 0.92 g of maleic anhydride modified ethylene propylene copolymer (produced by Mitsui Chemicals, Inc., Hi-wax 1105A) were added thereto. The mixture was heated to 80° C. while stirring to dissolve the surfactant, and then cooled to 55° C.

An 80 mass % aqueous solution of acrylic acid (92 g, 1.02 mol) was then placed in a 500-mL Erlenmeyer flask. While cooling the flask from the outside, a 30 mass % aqueous solution of sodium hydroxide (68.1 g, 0.51 mol) was added dropwise thereto to perform 50 mol % neutralization. To the thus neutralized solution, 1.15 g of a 2.0 mass % aqueous solution of 2,2'-azobis(2-amidinopropane)dihydrochloride as a radical polymerization initiator, 0.92 g of a 1.0 mass % aqueous solution of sodium hypophosphite monohydrate, and 51.6 g of ion-exchanged water were added, giving a monomer aqueous solution.

The entire quantity of this monomer aqueous solution was added to the cylindrical round-bottom flask. The flask was dipped in a 60° C. water bath to heat it to 58° C. The atmosphere inside the flask was replaced with nitrogen, followed by conducting a polymerization reaction. The contents reached the peak temperature (79° C.) 30 minutes after the initiation of the polymerization reaction. The flask was maintained in the state of being dipped in the 60° C. water bath for 0.5 hours, and the reaction was continued. The temperature of the internal solution after 0.5 hours was 59° C.

After the polymerization was completed, 30 g of a 3 mass % aqueous solution of disodium ethylenediaminetetraacetate was added to a slurry containing a hydrated gel of a water-soluble polyacrylic polymer. After stirring for 0.5 hours, the slurry was heated in a 125° C. oil bath. Azeotropic distillation of n-heptane and water was conducted to remove 138 g of water from the flask while refluxing the n-heptane. Thereafter, the n-heptane in the flask was removed by distillation to make the contents dry, obtaining 90.1 g of a water-soluble polymer composition.

[Preparation of a Composition for Forming a Plaster Layer]

0.25 parts by mass of tartaric acid was added to 86.55 parts by mass of distilled water, giving Liquid A.

Subsequently, a mixed solvent of 4 parts by mass of glycerol and 4 parts by mass of propylene glycol was placed in a 500-mL beaker, and 0.2 parts by mass of a dried aluminum hydroxide gel (produced by Kyowa Chemical Industry Co., Ltd.; model number: S-100, acid reactivity: 0.1 N—HCl=180 seconds) was added and dispersed, giving Liquid B.

While stirring Liquid B at 100 rpm using a pitched paddle having a blade diameter of 75 mm, 5 parts by mass of the aforementioned water-soluble polymer composition was added thereto in 2 seconds and stirring continued for 3 seconds. The total amount of the aforementioned Liquid A was then added thereto in 2 seconds. Thereafter, the mixture was stirred for 15 seconds, and then stirring was halted, obtaining a composition for forming a plaster layer.

Example 2

A 1,000-mL five-necked cylindrical round-bottom flask equipped with a reflux condenser, a dropping funnel, a nitrogen introduction tube, a stirrer, and a stirring blade was prepared. n-Heptane (340 g) was placed in this flask, and 0.92 g of sucrose stearate having HLB of 3 (produced by Mitsubishi-Kagaku Foods Corporation, Ryoto Sugar Ester S-370) and 0.92 g of a maleic anhydride modified ethylene-propylene copolymer (produced by Mitsui Chemicals, Inc., Hi-wax 1105A) were added thereto. The mixture was heated to 80° C. while stirring to dissolve the surfactant, and then cooled to 55° C.

An 80 mass % aqueous solution of acrylic acid (92 g, 1.02 mol) was then placed in a 500-mL Erlenmeyer flask. While cooling the flask from the outside, a 30 mass % aqueous solution of sodium hydroxide (68.1 g, 0.51 mol) was added dropwise thereto to perform 50 mol % neutralization. To the thus neutralized solution, 1.15 g of a 2.0 mass % aqueous solution of 2,2'-azobis(2-amidinopropane)dihydrochloride as a radical polymerization initiator, 0.92 g of a 1.0 mass % aqueous solution of sodium hypophosphite monohydrate, and 51.6 g of ion-exchanged water were added and dissolved, giving a monomer aqueous solution.

The entire quantity of this monomer aqueous solution was added to the cylindrical round-bottom flask. The flask was dipped in a 60° C. water bath to heat it to 58° C. The atmosphere inside the flask was replaced with nitrogen, followed by conducting a polymerization reaction. The contents reached the peak temperature (79° C.) 30 minutes after the initiation of the polymerization reaction. Thereafter, the flask was placed in a 55° C. water bath for 1 hour, and the reaction was continued. The temperature of the internal solution after 1 hour was 53° C.

After the polymerization was completed, 80 g of a 10 mass % aqueous solution of disodium ethylenediaminetetraacetate was added to a slurry containing a hydrated gel of water-soluble polyacrylic polymer. After stirring for 0.5 hours, the slurry was heated in a 125° C. oil bath. Azeotropic distillation of n-heptane and water was conducted to remove 181 g of water from the flask while refluxing the n-heptane. Thereafter, the n-heptane in the flask was removed by distillation to make the contents dry, obtaining 97.7 g of a water-soluble polyacrylic polymer composition.

Using the resulting water-soluble acrylic polymer composition, a composition for forming a plaster layer was prepared in the same manner as in Example 1.

Example 3

An 80 mass % aqueous solution of acrylic acid (27 g, 0.3 mol) was placed in a 300-mL Erlenmeyer flask. While cooling the flask from the outside, a 30 mass % aqueous solution of sodium hydroxide (20 g, 0.15 mol) was added dropwise thereto to perform 50 mol % neutralization. To the thus neutralized solution, 22.6 g of ion-exchanged water was added, giving a monomer aqueous solution.

To a 500-mL five-necked cylindrical round-bottom flask equipped with a reflux condenser, a dropping funnel, a nitrogen introduction tube, a stirrer, and a stirring blade, the entire quantity of this monomer aqueous solution was added. The atmosphere inside the flask was replaced with nitrogen, and the flask was dipped in a 60° C. water bath and heated to 58° C. 30 g of a 3 mass % aqueous solution of disodium ethylenediaminetetraacetate was added to the resulting solution, followed by stirring for 0.5 hours. Thereafter, 0.54 g of a 2.0 mass % aqueous solution of 2,2'-azobis(2-amidinopropane) dihydrochloride as a radical polymerization initiator, and 0.72 g of a 1.0 mass % aqueous solution of sodium hypophosphite monohydrate were added, followed by conducting a polymerization reaction. The contents became thicker one minute after the initiation of the polymerization reaction, and stirring was stopped when 2 minutes had passed. The contents reached the peak temperature (75° C.) 4 minutes after the initiation of the polymerization reaction. The flask was maintained in the state of being dipped in the 60° C. water bath for 3 hours, and the reaction was continued. The temperature of the internal solution after 3 hours was 58° C.

After the polymerization was completed, the unified hydrated gel of water-soluble polyacrylic polymer was dried at 120° C. for 2 hours. The dried polymer was pulverized and dried at 110° C. for 2 hours, obtaining 24.4 g of a water-soluble polyacrylic polymer composition.

Using the resulting water-soluble polyacrylic polymer composition, a composition for forming a plaster layer was produced in the same manner as in Example 1.

Example 4

A 1,000-mL five-necked cylindrical round-bottom flask equipped with a reflux condenser, a dropping funnel, a nitrogen introduction tube, a stirrer, and a stirring blade was prepared. n-Heptane (340 g) was placed in this flask, and 0.92 g of sucrose stearate having HLB of 3 (produced by Mitsubishi-Kagaku Foods Corporation, Ryoto Sugar Ester S-370) and 0.92 g of a maleic anhydride modified ethylene-propylene copolymer (produced by Mitsui Chemicals, Inc., Hi-wax 1105A) were added thereto. The mixture was heated to 80° C. while stirring to dissolve the surfactant, and then cooled to 55° C.

An 80 mass % aqueous solution of acrylic acid (92 g, 1.02 mol) was then placed in a 500-mL Erlenmeyer flask. While cooling the flask from the outside, a 30 mass % aqueous solution of sodium hydroxide (68.1 g, 0.51 mol) was added dropwise thereto to perform 50 mol % neutralization. To the thus neutralized solution, 1.15 g of a 2.0 mass % aqueous solution of 2,2'-azobis(2-amidinopropane)dihydrochloride as a radical polymerization initiator, 0.92 g of a 1.0 mass % aqueous solution of sodium hypophosphite monohydrate, and 51.6 g of ion-exchanged water were added, giving a monomer aqueous solution.

The entire quantity of this monomer aqueous solution was added to the cylindrical round-bottom flask. The flask was dipped in a 60° C. water bath to heat it to 58° C. The atmosphere inside the flask was replaced with nitrogen, followed by conducting a polymerization reaction. The contents reached the peak temperature (79° C.) 30 minutes after the initiation of the polymerization reaction. The flask was maintained in the state of being dipped in the 60° C. water bath for 0.5 hours, and the reaction was continued. The temperature of the internal solution after 0.5 hours was 59° C.

After the polymerization was completed, 100 g of a 10 mass % aqueous solution of disodium ethylenediaminetetraacetate was added to a slurry containing a hydrated gel of a water-soluble polyacrylic polymer. After stirring for 0.5 hours, the slurry was heated in a 125° C. oil bath. Azeotropic distillation of n-heptane and water was conducted to remove 199 g of water from the flask while refluxing the n-heptane. Thereafter, the n-heptane in the flask was removed by distillation to make the contents dry, obtaining 99.4 g of a water-soluble polyacrylic polymer composition.

Using the resulting water-soluble polyacrylic polymer composition, a composition for forming a plaster layer was produced in the same manner as in Example 1.

Comparative Example 1

A 1,000-mL five-necked cylindrical round-bottom flask equipped with a reflux condenser, a dropping funnel, a nitrogen introduction tube, a stirrer, and a stirring blade was prepared. n-Heptane (340 g) was placed in this flask, and 0.92 g of sucrose stearate having HLB of 3 (produced by Mitsubishi-Kagaku Foods Corporation, Ryoto Sugar Ester S-370) and 0.92 g of a maleic anhydride modified ethylene-propylene copolymer (produced by Mitsui Chemicals, Inc., Hi-wax 1105A) were added thereto. The mixture was heated to 80° C. while stirring to dissolve the surfactant, and then cooled to 55° C.

An 80 mass % aqueous solution of acrylic acid (92 g, 1.02 mol) was then placed in a 500-mL Erlenmeyer flask. While cooling the flask from the outside, a 30 mass % aqueous solution of sodium hydroxide (68.1 g, 0.51 mol) was added dropwise thereto to perform 50 mol % neutralization. To the thus neutralized solution, 1.15 g of a 2.0 mass % aqueous solution of 2,2'-azobis(2-amidinopropane)dihydrochloride as a radical polymerization initiator, 0.92 g of a 1.0 mass % aqueous solution of sodium hypophosphite monohydrate, and 51.6 g of ion-exchanged water were added and dissolved, giving a monomer aqueous solution.

The entire quantity of this monomer aqueous solution was added to the cylindrical round-bottom flask. The flask was dipped in a 60° C. water bath to heat it to 58° C. The atmosphere inside the flask was replaced with nitrogen, followed by conducting a polymerization reaction. The contents reached the peak temperature (79° C.) 30 minutes after the initiation of the polymerization reaction. The flask was maintained in the state of being dipped in the 60° C. water bath for 0.5 hours, and the reaction was continued. The temperature of the internal solution after 0.5 hours was 59° C.

After the polymerization was completed, a slurry containing a hydrated gel of a water-soluble polyacrylic polymer was heated in a 125° C. oil bath. Azeotropic distillation of n-heptane and water was conducted to remove 108 g of water from the flask while refluxing the n-heptane. Thereafter, the n-heptane in the flask was removed by distillation to make the contents dry, obtaining 89.1 g of a water-soluble polyacrylic polymer.

Using the resulting water-soluble polyacrylic polymer, a composition for forming a plaster layer was produced in the same manner as in Example 1.

Comparative Example 2

The water-soluble polyacrylic polymer obtained in Comparative Example 1 was used for preparing a gel-like composition as follows. That is, a composition for forming a plaster layer was produced in the same manner as in Example 1 except that 0.2 parts by mass of disodium ethylenediaminetetraacetate was added together with 5 parts by mass of water-soluble polyacrylic polymer.

The gel strengths of the compositions for forming a plaster layer obtained in Examples 1 to 4 and Comparative Examples 1 and 2 were evaluated by the procedure described below. Table 1 shows the evaluation results.

[Gel Aging]

Each of the above prepared compositions for forming a plaster layer (95 to 100 g) was placed in a polyethylene container (produced by AS ONE Corporation, product name: Tight Boy TB-2) and then placed in a thermo-hygrostat (produced by ESPEC Corp., product name: LHU-113) that was adjusted to 25° C. and relative humidity of 60%, and then allowed to age for a predetermined period of time (1, 2, 3, 6, 9, 12, 15, 18, 24, 30, 36, and 48 hours).

[Gel Strength]

The gel strengths immediately after production and after being aged for a predetermined period of time were measured using a curdmeter (produced by I TECHNO Co., Ltd., product name: Curdmeter MAX, model number: ME-303). The measurement conditions were as shown below:

Load: 100 g, diameter of pressure-sensitive shaft: 16 mm, carriage speed: 7 seconds/inch, and measurement mode: viscous.

Example 5

Preparation of Poultices

The composition for forming a plaster layer obtained in Example 1 was applied and spread over one surface of a polyester nonwoven fabric (produced by Japan Vilene Company, Ltd., product name: plaster base fabric) in such a manner that the thickness of the coating became 5 mm. The coated surface of the gel was covered with nylon film. The result was cut into a size of 100×50 mm, obtaining a poultice.

Examples 6 to 8 and Comparative Examples 3 and 4

Poultices were produced in the same manner as in Example 5 except that each of the compositions for forming plaster layers obtained in Examples 2 to 4 and Comparative Examples 1 and 2 shown in Table 1 were used.

The appearance of the poultices obtained in Examples 5 to 8 and Comparative Examples 3 and 4 was evaluated by the following procedure. Table 1 shows the evaluation results.

[Gel Condition]

In the production of poultices, the gel condition of the composition for forming a plaster layer immediately after application was evaluated by visually observing the presence or absence of unswollen lump.

A: No unswollen lump observed
B: Unswollen lump observed

TABLE 1

| | Gel Strength [N/m$^2$] Aging Time [hours] | | | | | | | | | | | | | | Gel |
|---|---|---|---|---|---|---|---|---|---|---|---|---|---|---|---|
| | 0 | 1 | 2 | 3 | 6 | 9 | 12 | 15 | 18 | 24 | 30 | 36 | 48 | | Condition |
| Example 1 | 147 | 98 | 99 | 101 | 223 | 321 | 405 | 448 | 458 | 480 | 484 | 484 | 487 | Example 5 | A |
| Example 2 | 143 | 96 | 96 | 98 | 98 | 99 | 105 | 158 | 270 | 401 | 430 | 444 | 452 | Example 6 | A |
| Example 3 | 111 | 93 | 94 | 95 | 95 | 148 | 255 | 360 | 432 | 467 | 471 | 480 | 480 | Example 7 | A |
| Example 4 | 141 | 95 | 97 | 95 | 98 | 97 | 98 | 99 | 189 | 340 | 389 | 390 | 390 | Example 8 | A |

TABLE 1-continued

| | Gel Strength [N/m$^2$] Aging Time [hours] | | | | | | | | | | | | | | Gel Condition |
|---|---|---|---|---|---|---|---|---|---|---|---|---|---|---|---|
| | 0 | 1 | 2 | 3 | 6 | 9 | 12 | 15 | 18 | 24 | 30 | 36 | 48 | | |
| Comparative Example 1 | 155 | 178 | 201 | 223 | 345 | 429 | 456 | 465 | 473 | 488 | 491 | 493 | 495 | Comparative Example 3 | A |
| Comparative Example 2 | 148 | 160 | 172 | 188 | 253 | 322 | 371 | 403 | 423 | 445 | 462 | 467 | 468 | Comparative Example 4 | B |

As is clear from Table 1, the water-soluble polyacrylic polymer compositions of Examples 1 to 4 exhibited a low gel strength of 200 N/m$^2$ or lower for more than 3 hours from the production of the composition for forming a plaster layer. Therefore, it is confirmed that these compositions have an appropriate induction period before the start of the hardening of the gel.

When the poultices of Examples 5 to 8 of the present invention are produced, unswollen lump is not observed in the composition for forming a plaster layer; therefore, the resulting poultices have an excellent appearance.

The invention claimed is:

1. A dried water-soluble polymer composition made by drying a hydrate gel comprising a water-soluble poly(meth) acrylic polymer and a gelation rate retarding agent,
    wherein the neutralization degree of the water-soluble poly (meth)acrylic polymer is 5 to 100 mol %,
    wherein the amount of the gelation rate retarding agent is 0.1 to 10 parts by mass relative to 100 parts by mass of the (meth)acrylic compound, which is at least one compound selected from the group consisting of (meth) acrylic acid and salts thereof, that is used to prepare the water-soluble poly(meth)acrylic polymer.

2. A method for producing a dried water-soluble polymer composition according to claim 1 comprising:
    polymerizing at least one (meth)acrylic compound selected from the group consisting of (meth)acrylic acid and salts thereof to obtain the hydrated gel of a water-soluble poly(meth) acrylic polymer;
    adding the gelation rate retarding agent before or while drying the resulting hydrated gel; and
    drying the result.

3. A method for producing a composition for forming a plaster layer of a skin patch comprising the method of claim 2, and further comprising a step of adding a polyvalent metal compound to the dried resulting water-soluble polymer composition.

4. A dried water-soluble polymer composition made by drying a hydrate gel comprising a water-soluble poly(meth) acrylic polymer and a gelation rate retarding agent,
    wherein the neutralization degree of the water-soluble poly (meth)acrylic polymer is 5 to 100 mol %,
    which is prepared by polymerizing at least one (meth) acrylic compound selected from the group consisting, of (meth)acrylic acid and salts thereof to obtain the hydrated the hydrated gel of a water-soluble poly(meth) acrylic polymer, adding the gelation rate retarding agent before or while drying the resulting hydrated gel, and drying the result,
    wherein the amount of the gelation rate retarding agent added is 0.1 to 10 parts by mass relative to 100 parts by mass of the (meth)acrylic compound, which is at least one compound selected from, the group consisting of (meth)acrylic acid and salts thereof, that is used to prepare the water-soluble poly(meth)acrylic polymer.

* * * * *

UNITED STATES PATENT AND TRADEMARK OFFICE
CERTIFICATE OF CORRECTION

| | | |
|---|---|---|
| PATENT NO. | : 8,906,980 B2 | Page 1 of 1 |
| APPLICATION NO. | : 13/383242 | |
| DATED | : December 9, 2014 | |
| INVENTOR(S) | : Kazuyuki Miura | |

It is certified that error appears in the above-identified patent and that said Letters Patent is hereby corrected as shown below:

On the Title page, item "(22) PCT Filed:" should read -Jul. 21, 2010-

Signed and Sealed this
Fourteenth Day of April, 2015

Michelle K. Lee
*Director of the United States Patent and Trademark Office*